(12) United States Patent
Choo et al.

(10) Patent No.: US 12,420,255 B2
(45) Date of Patent: Sep. 23, 2025

(54) APPARATUS AND METHOD FOR ESTERIFICATION REACTION

(71) Applicant: LG CHEM, LTD., Seoul (KR)

(72) Inventors: Yeon Uk Choo, Daejeon (KR); Sung Kyu Lee, Daejeon (KR); Hyoung Jun, Daejeon (KR); Hyun Kyu Kim, Daejeon (KR); Chan Hyu Jin, Daejeon (KR); Jin Sung Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 849 days.

(21) Appl. No.: 17/608,082

(22) PCT Filed: Sep. 18, 2020

(86) PCT No.: PCT/KR2020/012604
§ 371 (c)(1),
(2) Date: Nov. 1, 2021

(87) PCT Pub. No.: WO2021/060777
PCT Pub. Date: Apr. 1, 2021

(65) Prior Publication Data
US 2022/0314186 A1  Oct. 6, 2022

(30) Foreign Application Priority Data
Sep. 26, 2019 (KR) .................. 10-2019-0119165

(51) Int. Cl.
*B01J 19/18* (2006.01)
*B01J 19/00* (2006.01)
*C07C 67/08* (2006.01)

(52) U.S. Cl.
CPC ........... *B01J 19/0013* (2013.01); *B01J 19/18* (2013.01); *C07C 67/08* (2013.01);
(Continued)

(58) Field of Classification Search
None
See application file for complete search history.

(56) References Cited

U.S. PATENT DOCUMENTS 3,109,831 A   11/1963   Seiner
3,109,832 A   11/1963   Seiner
(Continued)

FOREIGN PATENT DOCUMENTS

CN   101626825 A   1/2010
CN   103127894 A   6/2013
(Continued)

OTHER PUBLICATIONS

Mustafizur Rahman et al., "The Plasticizer Market: An Assessment of Traditional Plasticizers and Research Trends to Meet New Challenges", Progress in Polymer Science 2004, 29, 1223-1248.
(Continued)

*Primary Examiner* — Jennifer A Leung
(74) *Attorney, Agent, or Firm* — Bryan Cave Leighton Paisner LLP (57) ABSTRACT

An esterification reaction apparatus and an esterification reaction method, the esterification reaction apparatus comprising a reaction tank having an accommodation part, in which a raw material containing carboxylic acid and alcohol is accommodated, a heating unit configured to individually heat partition regions that are partitioned into N regions in a vertical direction of the accommodation part, and a controller configured to control the heating unit so that only the partition regions in which a liquid is accommodated among the N partition regions are heated, thereby performing an esterification reaction of the raw material.

7 Claims, 5 Drawing Sheets

(52) U.S. Cl.
CPC ............... *B01J 2219/00081* (2013.01); *B01J 2219/00083* (2013.01); *B01J 2219/00159* (2013.01); *B01J 2219/00182* (2013.01)

(56) References Cited

U.S. PATENT DOCUMENTS

| | | | |
|---|---|---|---|
| 3,109,833 | A | 11/1963 | Seiner |
| 3,174,830 | A | 3/1965 | Watlz et al. |
| 3,392,088 | A * | 7/1968 | Johnson ............... B01D 3/4227 |
| | | | 700/270 |
| 4,289,895 | A | 9/1981 | Burkhardt et al. |
| 7,279,535 | B2 | 10/2007 | Konig et al. |
| 10,301,252 | B2 | 5/2019 | Horstmann et al. |
| 2008/0221296 | A1 * | 9/2008 | DeBruin ............... C08G 63/785 |
| | | | 528/272 |
| 2011/0033610 | A1 | 2/2011 | Bertram, Jr. |
| 2011/0104019 | A1 | 5/2011 | Debruin |
| 2016/0067665 | A1 | 3/2016 | Jiang et al. |
| 2018/0015435 | A1 | 1/2018 | Jiang et al. |
| 2019/0070931 | A1 | 3/2019 | Oh et al. |
| 2019/0255456 | A1 | 8/2019 | Banik |
| 2019/0263745 | A1 | 8/2019 | Lee et al. |

FOREIGN PATENT DOCUMENTS

| | | |
|---|---|---|
| CN | 203469501 U | 3/2014 |
| CN | 105368584 A | 3/2016 |
| CN | 106732289 A | 5/2017 |
| CN | 206463949 U | 9/2017 |
| CN | 207385473 U | 5/2018 |
| CN | 2073895473 U | 5/2018 |
| CN | 207899459 U | 9/2018 |
| CN | 109475785 A | 3/2019 |
| CN | 208727290 U | 4/2019 |
| FR | 1310102 A | 3/1963 |
| JP | 2010-520357 A | 6/2010 |
| JP | 2011140663 A * | 7/2011 |
| JP | 4867386 B | 2/2012 |
| JP | 2018-127603 A | 8/2018 |
| KR | 10-1999-0041717 A | 6/1999 |
| KR | 10-1999-0054928 A | 7/1999 |
| KR | 10-0928463 B | 11/2009 |
| KR | 10-2009-0129421 A | 12/2009 |
| KR | 10-2010-0033173 A | 3/2010 |
| KR | 10-2010-0137568 A | 12/2010 |
| KR | 10-2015-0143764 A | 12/2015 |
| KR | 10-2019-0027030 A | 3/2019 |
| KR | 10-2019-0027623 A | 3/2019 |
| WO | 2006-134884 A1 | 12/2006 |

OTHER PUBLICATIONS

Changri et al. (1996) "Production Method for Little Commodity of Chemical", Hunan Science and Technology Press, pp. 101-102.
Wenbang et al. (2006) "Pressure Vessel Design Guide", Yunnan Science and Technology Press, pp. 371-372.

* cited by examiner

APPARATUS AND METHOD FOR ESTERIFICATION REACTION

CROSS-REFERENCE TO RELATED APPLICATION

The present application is a U.S. National Stage Application of International Application No. PCT/KR2020/012604 filed on Sep. 18, 2020, which claims priority to and benefit of Korean Patent Application No. 10-2019-0119165, filed on Sep. 26, 2019, the disclosures of which are incorporated herein by reference in their entireties for all purposes as if fully set forth herein.

TECHNICAL FIELD

The present disclosure relates to an esterification reaction apparatus and an esterification reaction method.

BACKGROUND

A phthalate-based plasticizer accounts for 92% of the global plasticizer market until the 20th century (see Mustafizur Rahman and Christopher S. Brazel "The plasticizer market: an assessment of traditional plasticizers and research trends to meet new challenges" Progress in Polymer Science 2004, 29, 1223-1248). The phthalate-based plasticizer is an additive used for imparting flexibility, durability and cold resistance mainly to polyvinyl chloride (hereinafter, referred to as PVC) and lowering the viscosity during melting to improve processability. The phthalate-based plasticizer is added in various amounts to PVC and widely used in various applications from rigid products such as rigid pipes to soft products which may be used for such as food packaging materials, blood bags, flooring materials, etc. due to its soft and good flexibility. Therefore, it is more closely related to real life than any other material, and the direct contact with the human body may not avoidable.

However, in spite of the compatibility of the phthalate-based plasticizer with PVC and its excellent capability to impart flexibility, it has been argued recently about harmfulness of the PVC product containing the phthalate-based plasticizer that the phthalate-based plasticizer may leak from the PVC product when used in real life, and act as a presumed endocrine disrupting (environmental hormone) substance and a carcinogen, similar to the deleterious effects observed for heavy metals (see N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2008, 42, 7522-7527). Particularly, since the report about the leakage of di-(2-ethyl hexyl) phthalate (DEHP), which has been the most used phthalate-based plasticizer in the U.S in the 1960s, from the PVC product was published, the interest in environmental hormones have been boosted in the 1990s and global environmental regulations as well as various studies on hazards of the phthalate-based plasticizer to human have been implemented and started.

As a result, many researchers are conducting research to develop spill control technologies that suppress leakage of the phthalate plasticizer to not only significantly reduce the human risk but also meet environmental standards, as well as, develop a new non-phthalate-based plasticizer alternative that does not include phthalic anhydride in the manufacture of di(2-ethylhexyl) phthalate or develop a phthalate plasticizer that may replace di(2-ethylhexyl) phthalate and be used for industrial purposes due to the suppression of leakage of the plasticizer although being based on phthalate, in order to respond to environmental hormone problems and environmental regulations caused by the leakage of the phthalate plasticizer, particularly, di(2-ethylhexyl) phthalate.

As described above, development of materials that are free from environmental problems and which may replace di(2-ethylhexyl) phthalate having existing environmental problems, such as a diester-based plasticizer, is actively underway, and research on developing diester plasticizers with excellent physical properties, as well as research on facilities for manufacturing such plasticizers, is actively being conducted. Here, in terms of process design, more efficient, economical, and simple process design is required.

In order to manufacture the above-described diester plasticizer, the diester plasticizer is manufactured including a reaction process in which heat is applied to a raw material to perform an esterification reaction. However, there has been a problem that when a heat source is supplied to the raw material during the reaction process, heat transfer efficiency is low and the raw material is carbonized to generate foreign substances.

RELATED ARTS

Korean Patent Publication No. 10-2019-0027623

SUMMARY

One aspect of the present disclosure is an esterification reaction apparatus and esterification reaction method. The apparatus and method are capable of increasing heat transfer efficiency and preventing a raw material from being carbonized when a heat source is supplied to an accommodation part of a reaction tank so that the heat source is supplied to the raw material to cause an esterification reaction.

An esterification reaction apparatus comprises: a reaction tank having an accommodation part in which a raw material containing carboxylic acid and alcohol is accommodated; a heating unit configured to individually heat partition regions that are partitioned into N (N is an integer of 2 or more) regions in a vertical direction of the accommodation part; and a controller configured to control the heating unit so that only the partition regions, in which a liquid is accommodated, among the N partition regions are heated, thereby performing an esterification reaction of the raw material.

An esterification reaction method comprises: a supply process of supplying a raw material containing carboxylic acid and alcohol to an accommodation part of a reaction tank; a heating process of individually heating partition regions that are partitioned into N (N is an integer of 2 or more) regions in a vertical direction of the accommodation part through a heating unit; and a control process of controlling the heating unit through a controller during the heating process so that only the partition regions, in which a liquid is accommodated, among the N partition regions are heated, thereby performing an esterification reaction of the raw material.

ADVANTAGEOUS EFFECTS

According to the present disclosure, the heat transfer efficiency may increase by supplying the heat source to only the wet region, in which the liquid is accommodated, in the accommodation part of the reaction tank in which the esterification reaction occurs by applying the heat to the raw material containing carboxylic acid and alcohol. Here, the supply of the heat source to the dry region in which the liquid is not accommodated in the accommodation part may be blocked to prevent the foreign substances from being generated due to the carbonization of the raw material disposed in the dry region.

DETAILED DESCRIPTION

The objectives, specific advantages, and novel features of the present invention will become more apparent from the following detailed description taken in conjunction with the accompanying drawings. It should be noted that the reference numerals are added to the components of the drawings in the present specification with the same numerals as possible, even if they are illustrated in other drawings. Also, the present invention may be embodied in different forms and should not be construed as limited to the embodiments set forth herein. In the following description of the present invention, the detailed descriptions of related arts which may unnecessarily obscure the gist of the present invention will be omitted.

Figure 1:
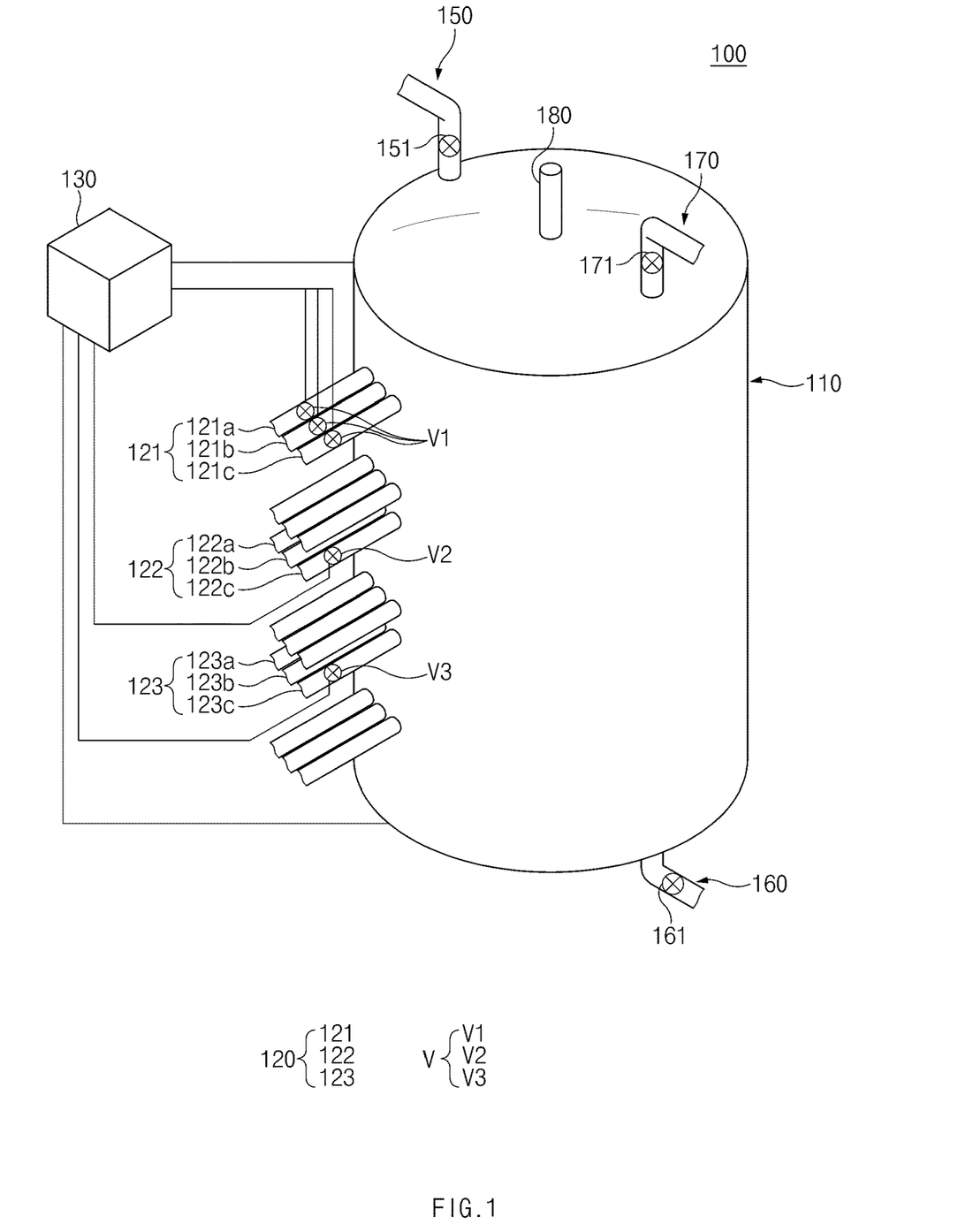
FIG. 1 is a perspective view of an esterification reaction apparatus according to an embodiment of the present invention.
Figure 2:
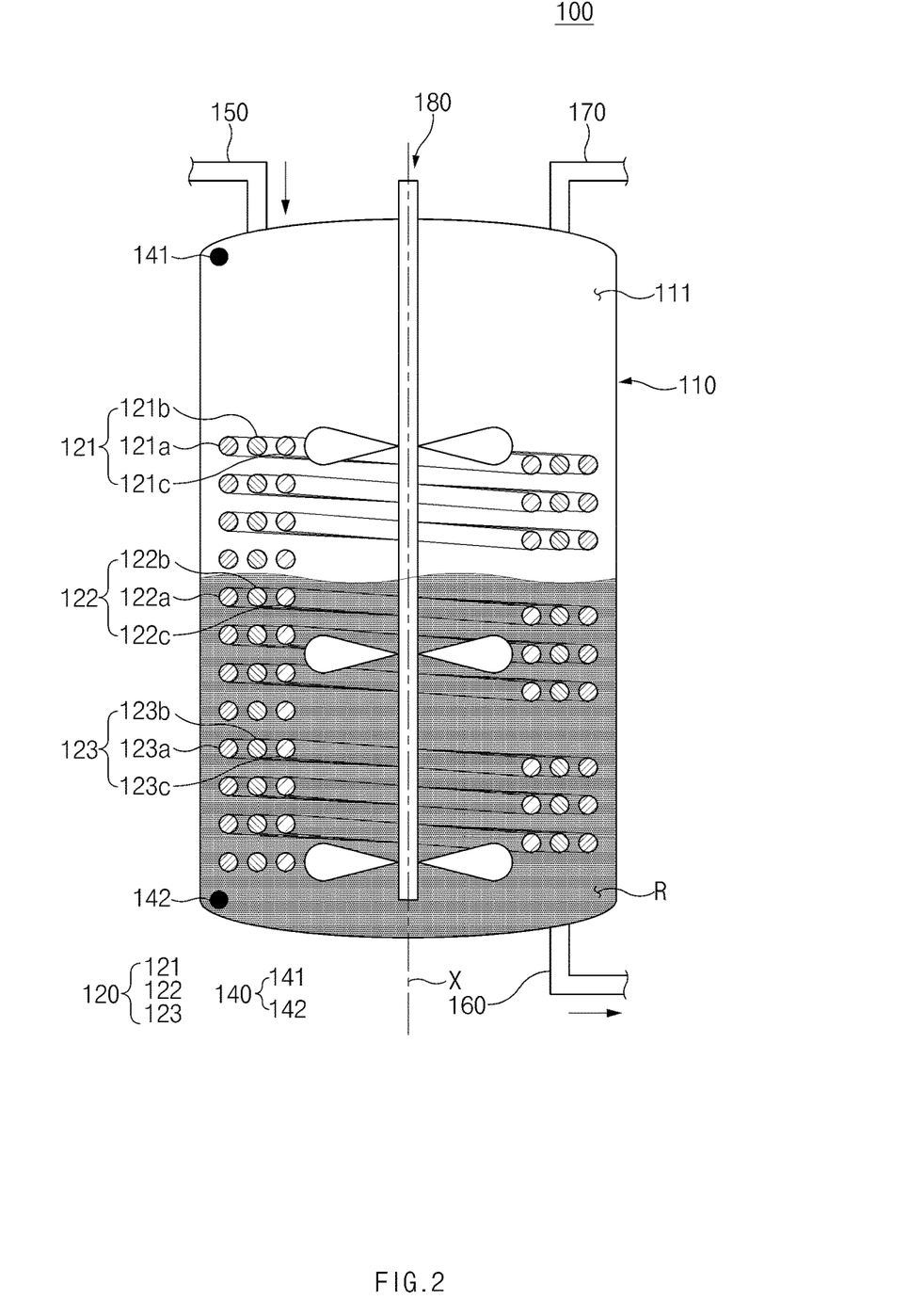
FIG. 2 is a cross-sectional view of the esterification reaction apparatus according to an embodiment of the present invention.
Figure 3:
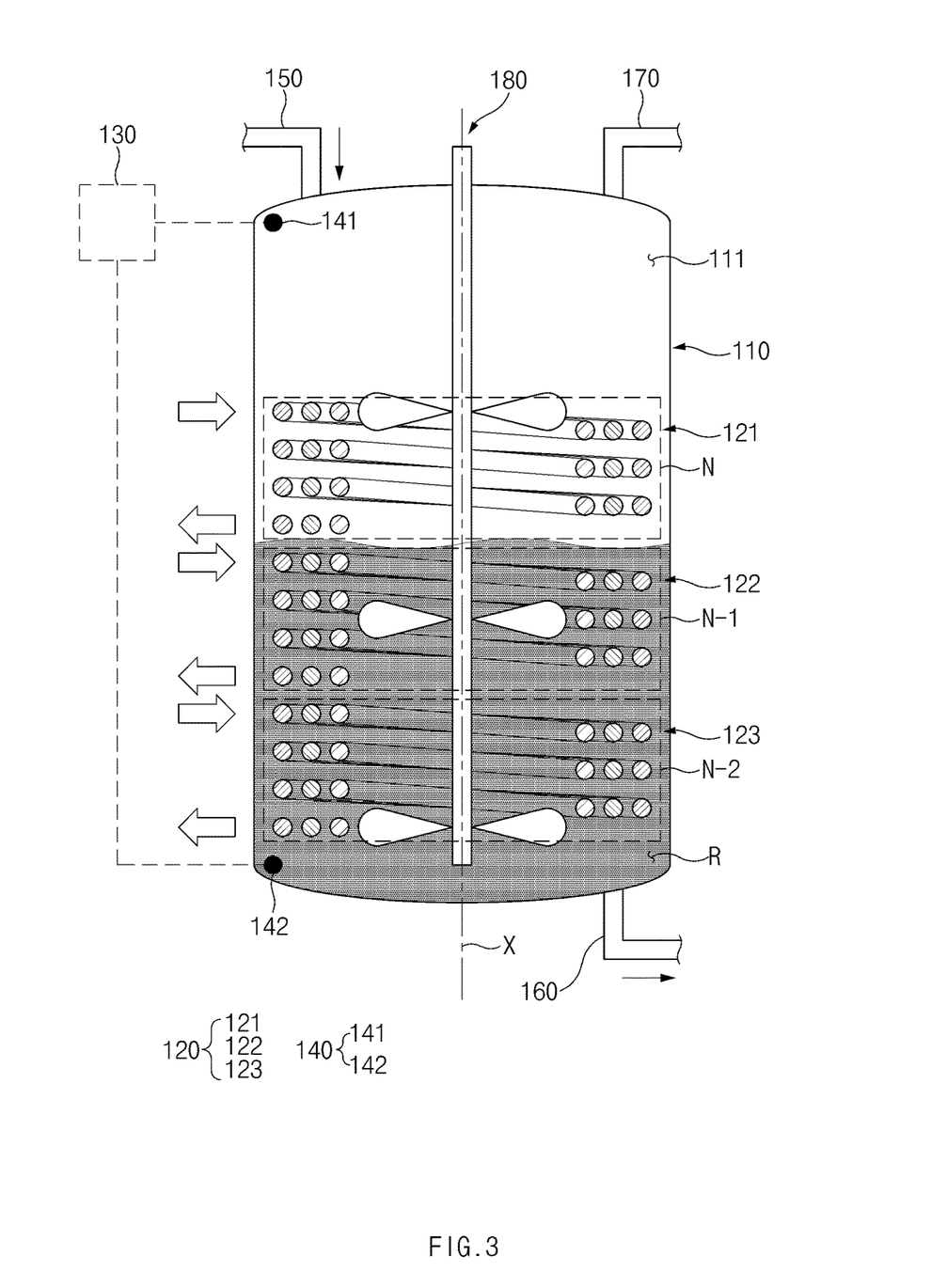
FIG. 3 is a conceptual cross-sectional view illustrating an example of the esterification reaction apparatus according to an embodiment of the present invention.

FIG. 1 is a perspective view of an esterification reaction apparatus according to an embodiment of the present invention, FIG. 2 is a cross-sectional view of the esterification reaction apparatus according to an embodiment of the present invention, and FIG. 3 is a conceptual cross-sectional view illustrating an example of the esterification reaction apparatus according to an embodiment of the present invention.

Figure 4:
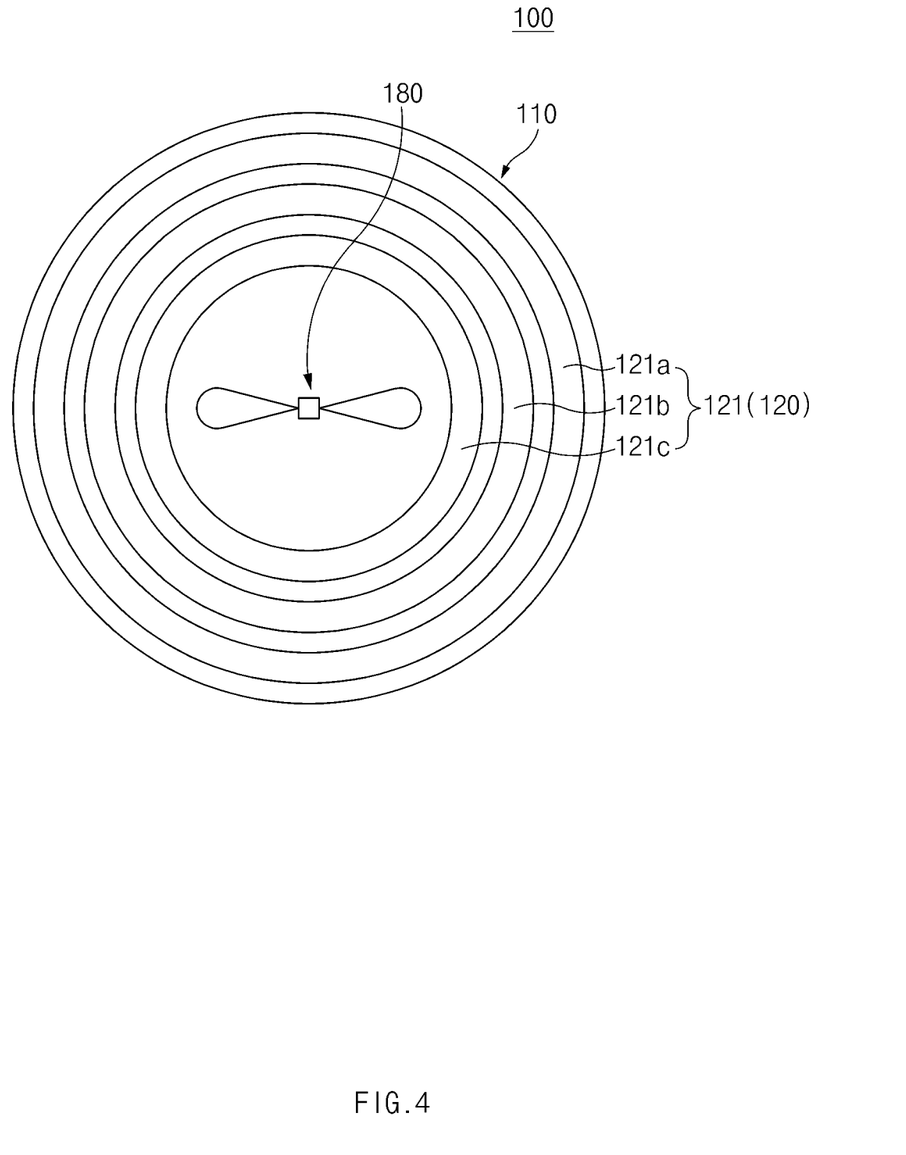
FIG. 4 is a plan view illustrating an example of the inside of a reaction tank in the esterification reaction apparatus according to an embodiment of the present invention.
Figure 5:
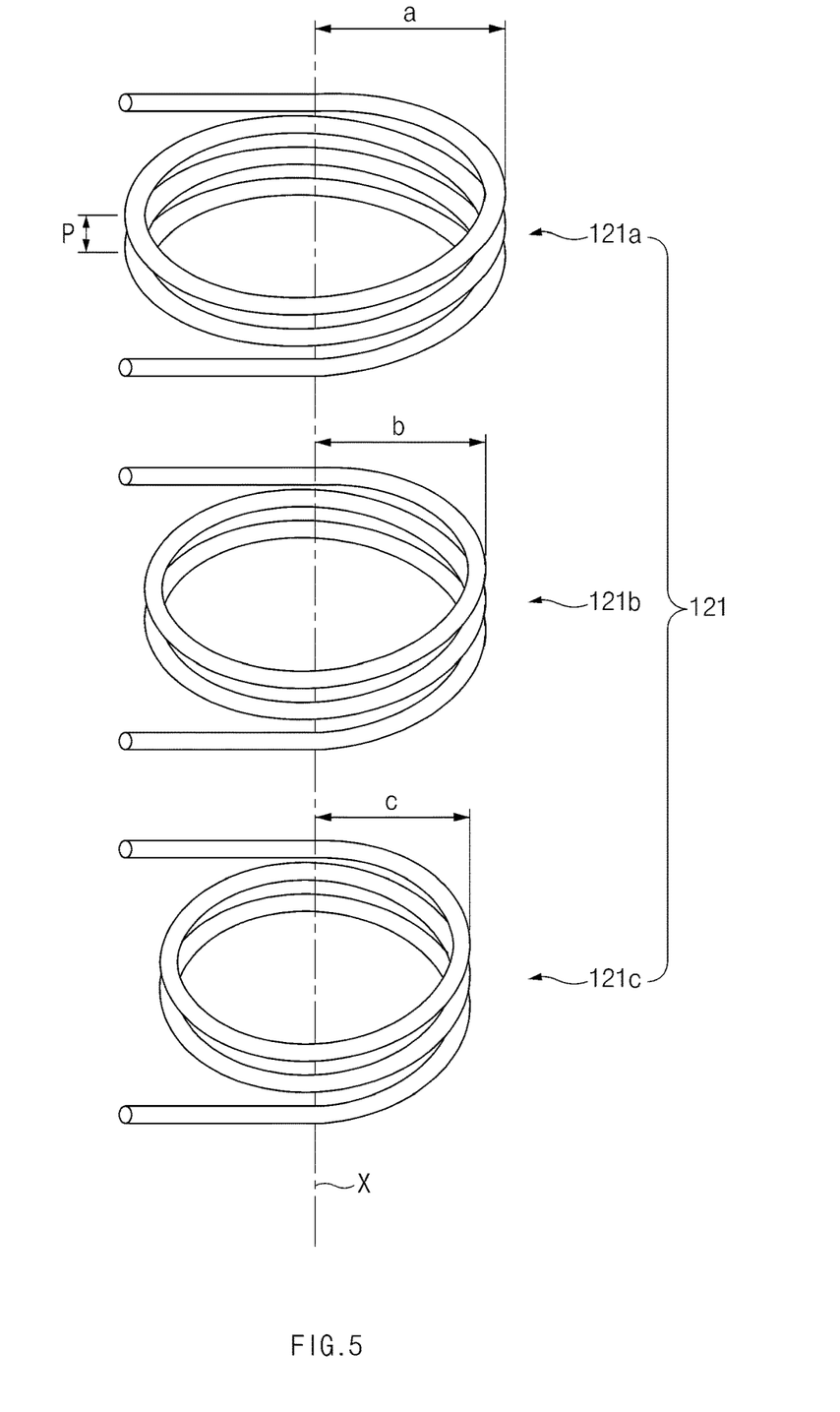
FIG. 5 is an exploded perspective view illustrating an example of a plurality of heat source supply tube, which is provided in a heat source supply part, in the esterification reaction apparatus according to an embodiment of the present invention.

FIG. 4 is a plan view illustrating an example of the inside of a reaction tank in the esterification reaction apparatus according to an embodiment of the present invention, and FIG. 5 is an exploded perspective view illustrating an example of a plurality of heat source supply tube, which is provided in a heat source supply part, in the esterification reaction apparatus according to an embodiment of the present invention.

Referring to FIGS. 1 to 3, an esterification reaction apparatus 100 according to an embodiment of the present invention comprises a reaction tank 110 in which an accommodation part 111 is formed, a heating unit 120 that individually heats partition regions N, N−1, and N−2 of the accommodation part 111, and a controller 130 controlling the heating unit 120 to perform an esterification reaction of a raw material. The esterification reaction apparatus 100 according to an embodiment of the present invention may further comprise a sensing unit 140 for sensing a liquid-accommodated state.

In more detail, the reaction tank 110 comprises an accommodation part 111 in which the raw material containing carboxylic acid and alcohol, which are supplied from the outside, is accommodated.

Here, the carboxylic acid may comprise, for example, one or more materials selected from the group consisting of terephthalic acid, phthalic acid, isophthalic acid, and cyclohexane dicarboxylic acid.

Here, the alcohol may have 3 to 10 alkyl carbon atoms.

The raw material may be supplied from the outside of the reaction tank 110 to the accommodation part 111 of the reaction tank 110 through a raw material supply part 150. Here, the raw material supplied to the accommodation part 111 of the reaction tank 110 may be stirred through a stirrer 180 disposed in the accommodation part 111 of the reaction tank 110. Here, a first control valve 151 is provided in the raw material supply part 150 to control the supply of the raw material.

The heating unit 120 may individually heat each of the partition regions N, N−1, and N−2, which are divided into N (N is an integer of 2 or more) regions in a vertical direction of the accommodation part 111. (Although three partition regions are shown in FIG. 3, the number of partition regions in the accommodation part of the present invention is not necessarily limited to three.)

Also, the heating unit 120 may comprise N heat source supply parts 121, 122, and 123, which are respectively provided in the N partition regions N, N−1, and N−2. Here, the heating unit 120 may further comprise a supply part valve V for opening and closing each of the N heat source supply parts 121, 122, and 123.

Furthermore, the heating unit 120 may comprise, for example, a first heat source supply part 121 disposed in an upper portion of the accommodation part 111 in the vertical direction, a second heat source supply part 122 disposed at a central portion of the accommodation part 111, and a third heat source supply part 123 disposed in a lower portion of the accommodation part 111, but the number of heat source supply parts 121, 122, and 123 of the heating unit 120 is not necessarily limited thereto. Here, the heating unit 120 may comprise, for example, a first supply part valve V1 for opening and closing the first heat source supply part 121, a second supply part valve V2 for opening and closing the second heat source supply part 122, and a third supply part valve V3 for opening and closing the third heat source supply part 123.

Referring to FIGS. 2 to 5, the heat source supply parts 121, 122, 123 may comprise heat source supply tubes 121a, 122a, 123a, 121b, 122b, 123b, 121c, 122c, and 123c, each of which has the form of a coil through which a high-temperature fluid as a heat source passes. Here, the high-temperature fluid may comprise, for example, steam. Here, the supply part valve V for opening and closing each of the heat source supply parts 121, 122, and 123 may be mounted on each of the heat source supply tubes 121a, 122a, 123a, 121b, 122b, 123b, 121c, 122c, and 123c in the heat source supply parts 121, 122, and 123.

Also, the heat source supply part 121, 122, and 123 may comprise a plurality of heat source supply tubes 121a, 122a, 123a, 121b, 122b, 123b, 121c, 122c, and 123c wound in the form of the coil around a vertical central axis X, which have different winding widths a, b, and c. Here, each of the N heat source supply parts 121, 122, and 123 may comprise the plurality of heat source supply tubes 121a, 122a, 123a, 121b, 122b, 123b, 121c, 122c, and 123c, each of which has the form of the coil. Thus, it is possible to uniformly heat the accommodation part 111 of the reaction tank 110. Here, the heat source supply parts 121, 122, and 123 disposed in the partition regions N, N−1, and N−2 of the accommodation part 111, which supplies the heat source, among the N heat source supply parts 121, 122, 123, may uniformly heat the corresponding partition regions N, N−1, and N−2.

Furthermore, the plurality of heat source supply tubes 121a, 122a, 123a, 121b, 122b, 123b, 121c, 122c, and 123c may comprise, for example, first heat source supply tubes 121a, 122a, and 123a and second heat source supply tubes 121b, 122b, and 123b, and third heat source supply tubes 121c, 122c, and 123c, which are arranged in an order of having the largest winding widths a, b, and c. That is, the first heat source supply tubes 121a, 122a, and 123a, each of which has the largest winding width a, are disposed in a spiral curve shape to be closest to the reaction tank 110, the third heat source supply tubes 121c, 122c, and 123c, each of which has the smallest winding width c, are disposed in a helical curve shape to be closest to the vertical central axis X of the accommodation part 111, and the second heat source supply tubes 121b, 122b, 123b, each of which has the winding width b, between the first heat source supply tubes 121a, 122a, 123a and the third heat source supply tubes 121c, 122c, and 123c are disposed in a spiral curve shape between the first heat source supply tubes 121a, 122a, 123a and the third heat source supply tubes 121c, 122c, and 123c. However, the number of heat source supply tubes 121a, 122a, 123a, 121b, 122b, 123b, 121c, 122c, and 123c of the heat source supply parts 121, 122, and 123 is not necessarily limited thereto.

Also, the plurality of heat source supply tubes 121a, 122a, 123a, 121b, 122b, 123b, 121c, 122c, and 123c may be provided, for example, in a shape of being wound multiple times around the vertical central axis X of the accommodation part 111 in the reaction tank 110.

Also, a coil pitch P of each of the heat source supply tubes 123a, 123b, and 123c disposed in the partition region N−2, which is disposed at the lowermost portion, among the N partition regions N, N−1, and N−2 of the accommodation part 111 may be equal to or less than a coil pitch P of each of the heat source supply tubes 121a, 122a, 121b, 122b, 121c, and 122c, which are disposed in the remaining regions N and N−1. Therefore, heat transfer efficiency in the lowermost partition region N−2 of the accommodation part 111, in which the liquid raw material is accommodated always, may be more improved to improve the reaction efficiency.

The carboxylic acid and the alcohol, which are heated through the heating unit 120, may cause an esterification reaction to generate an ester-based material and water as products of the esterification reaction. Here, the liquid ester-based material may be generated by the esterification reaction and then be discharged to the outside of the reaction tank 110 through a liquid material discharge part 160, and the water may be generated, but be vaporized to be discharged to the outside of the reaction tank 110 through a vaporized material discharge part 170.

For example, the liquid material discharge part 160 may be connected to a lower portion of the reaction tank 110, and the vaporized material discharge part 170 may be connected to an upper portion of the reaction tank 110.

Also, a second control valve 161 may be provided in the liquid material discharge part 160 to control the discharge of the generated liquid material, and a third control valve 171 may be provided in the vaporized material discharge part 170 to control the discharge of the vaporized material. (see FIG. 1)

Referring to FIG. 3, the sensing unit 140 may sense a liquid-accommodated state in the N partition regions N, N−1, and N−2 of the accommodation part 111.

In addition, the sensing unit 140 may transmit the sensed liquid-accommodated state information to the controller 130.

Furthermore, the sensing unit 140 may comprise liquid level sensors 141 and 142 that are disposed inside the reaction tank 110 to measure an accommodation height (level) of a liquid R accommodated in the accommodation part 111.

Here, the sensing unit 140 may comprise a first liquid level sensor 141 disposed in the upper portion of the accommodation part 111 of the reaction tank 110 and a second liquid level sensor 142 disposed in the lower portion of the accommodation part 111 of the reaction tank 110.

Referring to FIGS. 1 and 3, the controller 130 may control the heating unit 120 to heat only the partition region N, N−1, and N−2, in which the liquid R is disposed, among the N partition regions N, N−1, and N−2. Here, the controller 130 may control the supply part valve V for opening and closing each of the N heat source supply parts 121, 122, and 123 to control the supply of the heat source of the heating unit 120.

In addition, the controller 130 may determine whether the liquid is accommodated in each of the partition regions N, N−1, and N−2 of the accommodation part 111 through sensed accommodation level values of the accommodated liquid R, which are sensed through the sensing unit 140. Here, the controller 130 may control the supply of the high-temperature liquid so that the high-temperature liquid is supplied to the heat source supply tubes 121a, 122a, 123a, 121b, 122b, 123b, 121c, 122c, and 123c of the partition regions N, N−1, N−2, which are determined to contain the liquid R, among the N partition regions N, N−1, N−2, and the supply of the high-temperature liquid to the heat source supply tubes 121a, 122a, 123a, 121b, 122b, 123b, 121c, 122c, and 123c of the partition regions N, N−1, N−2, which are determined to contain no liquid R, among the N partition regions N, N−1, N−2 is blocked.

Here, the partition regions N, N−1, and N−2, which are heated by supplying the high-temperature fluid to the heat source supply tubes 121a, 122a, 123a, 121b, 122b, 123b, 121c, 122c, and 123c, may be heated, for example, at a temperature of 150° C. to 230° C. Here, particularly, the partition regions N, N−1, and N−2, which are heated by supplying the high-temperature fluid to the heat source supply tubes 121a, 122a, 123a, 121b, 122b, 123b, 121c, 122c, and 123c, may be heated, for example, at a temperature of 180° C. Here, the opening and closing of each of the supply part valves V1, V2, and V3 may be controlled by the controller 130 so that the corresponding partition regions N, N−1, and N−2 are individually heated through the heat source supply tubes 121a, 122a, 123a, 121b, 122b, 123b, 121c, 122c, and 123c, which constituent the heating unit 120.

The controller 130 may be connected to the raw material supply part 150 through the first control valve 151, connected to the liquid martial discharge part 160 through the second control valve 161, and connected to the vaporized material discharge part 170 through the third control valve 171 to control the first control valve 151, the second control valve 161, and the third control valve 171. (Here, since the technology in which the valve is electrically controlled through the controller is a known technology, descriptions of the operation principle and control principle of the valve will be omitted)

Referring to FIGS. 1 to 3, in the esterification reaction apparatus 100, which comprises the above-described constituents, according to an embodiment of the present invention, the accommodation part 111 of the reaction tank 110 may be partitioned into N regions in which the heat is applied to the raw material containing carboxylic acid and alcohol to cause the esterification reaction, and the partition regions N, N−1, and N−2 may be individually heated through the heating unit 120. Here, the controller may control the heating unit 120 so that only the partition regions N, N−1, and N−2, in which the liquid R is accommodated, are heated.

Accordingly, the heat source may be supplied to only the wet region, in which the liquid R is accommodated, among the N partition regions N, N−1, and N−2 of the accommodation part 111 to significantly improve the heat transfer efficiency. That is, when the heat is applied to the raw material mixed with liquid carboxylic acid and alcohol to cause the esterification reaction, only the region in which the raw material solution, in which the carboxylic acid and the alcohol are mixed, is accommodated to cause the esterification reaction may be heated to prevent a problem in which the heat source is unnecessarily applied to the region in which the raw material solution is not accommodated so as not to cause the esterification reaction, to deteriorate the efficiency.

Also, the supply of the heat source to a dry region in which the liquid R is not accommodated may be blocked to prevent the raw material from being carbonized. That is, when the heat is applied to the raw material mixed with the liquid carboxylic acid and the alcohol to cause the esterification reaction, a problem, in which the heat is applied to a solid or gaseous material in the raw material to carbonize the solid or gaseous material, thereby generating foreign substances, may be prevented by blocking the supply of the heat source to the dry region.

Hereinafter, an esterification reaction method according to an embodiment of the present invention will be described.

Referring to FIGS. 1 to 3, an esterification reaction method according to an embodiment of the present invention comprises a supply process of supplying a raw material to an accommodation part 111 of a reaction tank 110, a heating process of heating partition regions N, N−1, and N−2 of the accommodation part 111, and a control process of controlling a heating unit 120 through a controller during the heating process to perform an esterification reaction. In addition, the esterification reaction method according to an embodiment of the present invention may further comprise a sensing process of sensing a liquid-accommodated state.

In more detail, in the supply process, the raw material containing carboxylic acid and alcohol may be supplied to the accommodation part 111 of the reaction tank 110.

In addition, in the supply process, for example, the liquid carboxylic acid and alcohol may be mixed and supplied to the accommodation part 111 of the reaction tank 110 through a raw material supply part 150. Here, a first control valve 151 is provided in the raw material supply part 150 to control the supply of the raw material.

The carboxylic acid may comprise, for example, one or more materials selected from the group consisting of terephthalic acid, phthalic acid, isophthalic acid, and cyclohexane dicarboxylic acid.

The alcohol may have 3 to 10 alkyl carbon atoms.

Also, a molar ratio of an amount of added carboxylic acid and a total amount of added alcohol to the accommodation part 111 of the reaction tank 110 during the supply process may be, for example, 1:2 to 1:5.

In the heating process, the partition regions N, N−1, and N−2 that are divided into N (N is an integer of 2 or more) regions in a vertical direction of the accommodation part 111 may be individually heated through the heating unit 120.

In addition, in the heating process, the partition regions N, N−1, and N−2 of the accommodation part 111 may be individually heated through N heat source supply parts 121, 122, and 123 constituting the heating unit 120, which are respectively provided in N partition regions N, N−1, and N−2.

Furthermore, the partition regions N, N−1, and N−2 of the accommodation part 111 may be individually heated using heat source supply tubes 121*a*, 122*a*, 123*a*, 121*b*, 122*b*, 123*b*, 121*c*, 122*c*, and 123*c*, each of which has the form of a coil and through which a high-temperature fluid, that is the heat source, passes, in the heat source supply parts 121, 122, and 123.

In addition, in the heating process, steam may be used as the high-temperature fluid passing through the heat source supply tubes 121*a*, 122*a*, 123*a*, 121*b*, 122*b*, 123*b*, 121*c*, 122*c*, and 123*c*.

The carboxylic acid and the alcohol may cause the esterification reaction through the heating process to generate an ester-based material and water as products of the esterification reaction.

Here, the liquid ester-based material, which is generated through the esterification reaction, may be discharged to the outside of the reaction tank 110 through a liquid material discharge part 160, and the water may be vaporized to be discharged to the outside of the reaction tank 110 through a vaporized material discharge part 170.

For example, the liquid material discharge part 160 may be connected to a lower portion of the reaction tank 110, and the vaporized material discharge part 170 may be connected to an upper portion of the reaction tank 110.

Also, a second control valve 161 may be provided in the liquid material discharge part 160 to control the discharge of the generated liquid material, and a third control valve 171 may be provided in the vaporized material discharge part 170 to control the discharge of the vaporized material such as the vaporized alcohol and water.

In the sensing process, the liquid-accommodated state in the N partition regions N, N−1, and N−2 may be individually sensed through a sensing unit 140. Here, in the sensing process, the liquid-accommodated state information sensed through the sensing unit 140 may be transmitted to the controller 130.

In addition, in the sensing process, an accommodated level (height) of a liquid R accommodated in the accommodation part 111 may be sensed through a liquid level sensor disposed inside the reaction tank 110, which is the sensing unit 140.

In the control process, the heating unit 120 may be controlled through the controller 130 during the heating process so that only the partition regions N, N−1, and N−2, in which the liquid R is accommodated, among the N partition regions N, N−1, and N−2 are heated by the heating unit 120.

In addition, in the control process, the controller 130 may determine whether the liquid is accommodated in each of the partition regions N, N−1, and N−2 of the accommodation part 111 through sensed accommodation level values of the accommodated liquid R, which are sensed in the sensing process. Here, in the control process, the controller 130 may control the supply of the high-temperature liquid so that the high-temperature liquid is supplied to the heat source supply tubes 121*a*, 122*a*, 123*a*, 121*b*, 122*b*, 123*b*, 121*c*, 122*c*, and 123*c* of the partition regions N, N–1, N–2, which are determined to contain the liquid R, among the N partition regions N, N–1, N–2, and the supply of the high-temperature liquid to the heat source supply tubes 121*a*, 122*a*, 123*a*, 121*b*, 122*b*, 123*b*, 121*c*, 122*c*, and 123*c* of the partition regions N, N–1, N–2, which are determined to contain no liquid R, among the N partition regions N, N–1, N–2 is blocked.

Furthermore, in the control process, for example, the controller 130 may control opening and closing of a supply part valve V for opening and closing each of the heat source supply tubes 121*a*, 122*a*, 123*a*, 121*b*, 122*b*, 123*b*, 121*c*, 122*c*, and 123*c* to control supply of the high-temperature fluid to the heat source supply tubes 121*a*, 122*a*, 123*a*, 121*b*, 122*b*, 123*b*, 121*c*, 122*c*, and 123*c*. Here, in the control process, particularly, the supply part valve V disposed in each of the heat source supply tubes 121*a*, 122*a*, 123*a*, 121*b*, 122*b*, 123*b*, 121*c*, 122*c*, and 123*c* of the partition regions N, N–1, N–2, which are determined to contain the liquid R, among the N partition regions N, N–1, N–2 may be opened to supply a high-temperature fluid, and the supply part valve V disposed in each of the heat source supply tubes 121*a*, 122*a*, 123*a*, 121*b*, 122*b*, 123*b*, 121*c*, 122*c*, and 123*c* of the partition regions N, N–1, N–2, which are determined to contain no liquid R, among the N partition regions N, N–1, N–2 may be closed to block the supply of the high-temperature fluid.

The controller 130 may be connected to the raw material supply part 150 through the first control valve 151, connected to the liquid martial discharge part 160 through the second control valve 161, and connected to the vaporized material discharge part 170 through the third control valve 171 to control the first control valve 151, the second control valve 161, and the third control valve 171. Accordingly, in the control process, a supply amount of raw material, an amount of generated liquid material, and an amount of vaporized material may be controlled through the controller 130. Here, in the control process, the accommodated level (height) of the liquid R accommodated in the accommodation part 111 of the reaction tank 110 may be controlled through the controller 130. Therefore, In the control process, the accommodated level (height) of the liquid R may be controlled through the controller 130 to correspond to an appropriate height of each of the N partition regions N, N–1, and N–2 in the accommodation part 111, which are individually heated by the heat source supply parts 121, 122, and 123.

While the present invention has been particularly shown and described with reference to exemplary embodiments thereof, it is to be understood that the scope of the present invention is not limited to the esterification reaction apparatus and the esterification reaction method according to the present invention. It will be understood by those of ordinary skill in the art that various changes in form and details may be made therein without departing from the spirit and scope of the present invention.

Furthermore, the scope of protection of the present invention will be clarified by the appended claims.

DESCRIPTION OF REFERENCE NUMERALS

100: Esterification reaction apparatus
110: Reaction tank
111: Accommodation part
120: heating unit
121: First heat source supply part
121*a*: first heat source supply tube
121*b*: Second heat source supply tube
121*c*: Third heat source supply tube
122: Second heat source supply part
122*a*: First heat source supply tube
122*b*: Second heat source supply tube
122*c*: Third heat source supply tube
123: Third heat source supply part
123*a*: First heat source supply tube
123*b*: Second heat source supply tube
123*c*: Third heat source supply tube
130: Controller
140: Sensing unit
141: First liquid level sensor
142: Second liquid level sensor
150: Raw material supply part
151: First control valve
160: Liquid material discharge part
161: Second control valve
170: Vaporized material discharge part
171: Third control valve
180: Stirrer
R: Liquid
V: Supply part valve
V1: First supply part valve
V2: Second supply part valve
V3: Third supply part valve
X; Central axis

The invention claimed is:

1. An esterification reaction apparatus, comprising:
a reaction tank having an accommodation part in which a raw material containing carboxylic acid and alcohol is accommodated;
a heating unit configured to individually heat partition regions that are partitioned into N regions in a vertical direction of the accommodation part, where N is an integer of 2 or more; and
a controller configured to control the heating unit so that only the partition regions in which a liquid of the raw material is accommodated among the N partition regions are heated,
thereby performing an esterification reaction of the raw material,
wherein the heating unit comprises N heat source supply parts, which are respectively provided in the N partition regions,
wherein each of the heat source supply parts comprises a heat source supply tube therein which has the form of a coil and through which a high-temperature fluid passes, wherein the high-temperature fluid is a heat source,
wherein a coil pitch of the heat source supply tube disposed in the partition region, which is disposed at the lowermost portion, among the N partition regions is less than a coil pitch of the heat source supply tubes, which are disposed in the remaining regions.

2. The esterification reaction apparatus of claim 1, wherein the heat source supply parts comprise a plurality of heat source supply tubes wound in the form of the coil, which have different winding widths from a center axis in the vertical direction of the accommodation part from each other.

3. The esterification reaction apparatus of claim 2, wherein the plurality of heat source supply tubes are provided in a shape of being wound multiple times around the center axis in the vertical direction of the accommodation part in the reaction tank.

4. The esterification reaction apparatus of claim 1, wherein the high-temperature fluid comprises steam.

5. The esterification reaction apparatus of claim 1, further comprising a sensing unit configured to sense a liquid-accommodated state in the N partition regions,
  wherein the sensing unit is configured to transmit information of the sensed liquid-accommodated state to the controller.

6. The esterification reaction apparatus of claim 5, wherein the sensing unit comprises a liquid level sensor disposed in the reaction tank to measure an accommodation height (level) of the liquid accommodated in the accommodation part.

7. The esterification reaction apparatus of claim 6, wherein the controller is configured to determine whether the liquid is accommodated in each of the N partition regions of the accommodation part through sensed accommodation level values of the accommodated liquid sensed through the sensing unit so that the high-temperature fluid is supplied to the heat source supply tubes of the partition regions which are determined to contain the liquid among the N partition regions, and supplying the high-temperature fluid to the heat source supply tubes of the partition regions which are determined to contain no liquid among the N partition regions is blocked.

* * * * *